US008709746B2

(12) United States Patent
Cellier et al.

(10) Patent No.: US 8,709,746 B2
(45) Date of Patent: Apr. 29, 2014

(54) REACTION MEDIUM FOR DETECTING AND/OR IDENTIFYING BACTERIA OF THE *LEGIONELLA* GENUS

(75) Inventors: Marie Cellier, La Balme les Grottes (FR); Sylvain Orenga, Neuville sur Ain (FR); Denis Robichon, Blyes (FR); Veronique Sauvonnet, Courtenay (FR)

(73) Assignee: bioMerieux, Marcy l'Etoile (FR)

( * ) Notice: Subject to any disclaimer, the term of this patent is extended or adjusted under 35 U.S.C. 154(b) by 266 days.

(21) Appl. No.: 13/120,050

(22) PCT Filed: Oct. 14, 2009

(86) PCT No.: PCT/FR2009/051961
§ 371 (c)(1),
(2), (4) Date: Mar. 21, 2011

(87) PCT Pub. No.: WO2010/043818
PCT Pub. Date: Apr. 22, 2010

(65) Prior Publication Data
US 2011/0171667 A1 Jul. 14, 2011

(30) Foreign Application Priority Data
Oct. 17, 2008 (FR) ...................................... 08 57078

(51) Int. Cl.
*C12Q 1/04* (2006.01)

(52) U.S. Cl.
USPC .......................... 435/34; 435/7.32; 435/253.6

(58) Field of Classification Search
None
See application file for complete search history.

(56) References Cited

U.S. PATENT DOCUMENTS

| 5,187,066 | A | * | 2/1993 | Becker et al. | ................. 435/7.36 |
| 5,314,855 | A | * | 5/1994 | Thorpe et al. | .................... 502/80 |
| 2004/0029212 | A1 | | 2/2004 | Rodriguez Martinez et al. | |

FOREIGN PATENT DOCUMENTS

| FR | 755.371 | 11/1933 |
| FR | 755.373 | 11/1933 |
| WO | WO 93/04077 A1 | 3/1993 |
| WO | WO 00/28073 A1 | 5/2000 |

OTHER PUBLICATIONS

Murdoch, D.R., Medical Microbiology, 2003, vol. 36, p. 64-69.*
MICROLAB, Microgen Bioproducts Newsletter, 2002, No. 9, p. 1-3.*
Reglier-Poupet et al., Journal of Medical Microbiology, 2008, vol. 57, p. 310-315.*
International Search Report issued in International Patent Application No. PCT/FR2009/051961 dated Aug. 3, 2010 (with translation).
Written Opinion issued in International Patent Application No. PCT/FR2009/051961 dated Aug. 3, 2010.
Xiu-Rong et al., "Study on the mechanism of the interaction between montmorillonite and bacterium," *Acta Pharmaceulica Sinica*, 2002, pp. 718-720, vol. 37, No. 9.
Feeley et al., "Charcoal-yeast extract agar: primary isolation medium for Legionella pneumophila," *Journal of Clinical Microbiology*, Oct. 1979, pp. 437-441, vol. 10, No. 4.
Edelstein, "Improved semiselective medium for isolation of *Legionella pneumophila* from contaminated clinical and environmental specimens," *Journal of Clinical Microbiology*, Sep. 1981, pp. 298-303, vol. 14, No. 3.
Lee et al., "Growth of 28 *Legionella* species on selective culture media: a comparative study," *Journal of Clinical Microbiology, Microbiology*, Oct. 1993, pp. 2764-2768, vol. 31, No. 10.
Edelstein et al, "Comparison of three buffers used in the formulation of buffered charcoal yeast extract medium," *Journal of Clinical Microbiology*, Dec. 1993, pp. 3329-3330, vol. 31, No. 12.
Morrill et al., "Increased recovery of *Legionella micdadei* and *Legionella bozemanii* on buffered charcoal yeast extract agar supplemented with albumin," *Journal of Clinical Microbiology*, Mar. 1990, pp. 616-618, vol. 28, No. 3.

* cited by examiner

*Primary Examiner* — Kade Ariani
(74) *Attorney, Agent, or Firm* — Oliff PLC

(57) ABSTRACT

A reaction medium for the culture and/or detection and/or identification of bacteria of the *Legionella* genus includes at least one siliceous compound, where the siliceous compound is a nonpolar silica. A method for detecting and/or identifying bacteria of the *Legionella* genus, includes bringing a sample that may contain bacteria of the *Legionella* genus into contact with a reaction medium comprising at least one siliceous compound, incubating, and detecting the presence of bacteria of the *Legionella* genus.

23 Claims, No Drawings

REACTION MEDIUM FOR DETECTING AND/OR IDENTIFYING BACTERIA OF THE LEGIONELLA GENUS

This Application is a national stage entry of PCT/FR2009/051961, filed Oct. 14, 2009, which claims priority to FR 0857078, filed Oct. 17, 2008.

The present invention relates to a reaction medium for legionellae, and also to the use of such a medium and to a method using this medium.

Legionellae (*Legionella* sp) are bacteria of hydric environments (natural ecosystems and water distribution networks) capable of causing infections, sometimes lethal infections, in humans. Several species of the *Legionella* genus have been demonstrated in humans, but the most important is *Legionella pneumophila* (*L. pneumophila*), which is responsible for approximately 90% of cases of legionellosis. Other species, such as *L. jordanis*, are generally isolated in immunodepressed individuals. Legionellosis (or legionnaire's disease) is a respiratory disease characterized by severe acute pneumopathy, of which infection is acquired by inhalation of aerosols contaminated with *Legionella*, for instance cooling towers, air-conditioning systems, health spas, showers, etc. After an incubation period of 2 to 10 days, patients exhibit a flu-like syndrome. This is followed by a high fever, pleuresy and a severe cough, associated with gastrointestinal problems (diarrhea, vomiting) or even sometimes neurological problems (delirium, drowsiness, confusion). In 2005, more than 1500 cases were reported in France and approximately 5700 in Europe; in the United States, the CDC (Centers for Disease Control and Prevention) estimates that there are 8000 to 18 000 cases of legionellosis per year.

The diagnosis of legionellosis is very complex since the disease is atypical: a classic pneumopathy, there is nothing specific about it. Mortality is 20% of cases on average, rather low in community cases but, on the other hand, high in nosocomial cases. Early diagnosis is essential in order to provide the patient with suitable treatment. Diagnosis can be carried out according to the following methods:

identification by a direct immunofluorescence method. Carried out on a sample with antibodies against the main *L. pneumophila* serogroups, this method makes it possible to demonstrate the soluble antigens. The methods mainly used are ELISA (Enzyme Linked ImmunoSorbant Assay), RIA (RadioImmunology Assay) or ICM (ImmunoChromatography on Membrane). The major drawback of these techniques is that they make it possible to detect only the possible presence of certain *L. pneumophila* serogroups;

serological diagnosis of antibodies against LPS O antigen by indirect immunofluorescence. This method makes it possible to identify only *L. pneumophila* serogroup 1 and has the risk of many false positives due to cross reactions with mycobacteria, leptospira, *Chlamydia, Mycoplasma, Pseudomonas, Flavobacterium*, etc;

bacteriological identification by the culture method. It is difficult to grow legionellae. This is because they do not culture on blood agars, the pH must be strictly controlled (6.9+/−0.2) and the requirements of the bacteria must be met. Thus, cultures are generally performed on a BCYE (Buffered Charcoal Yeast Extract) agar supplemented with ACES buffer, with L-cysteine and with iron; these last two elements being essential growth factors; or GVPC agar. The colonies can be observed from 48 h of incubation at 37° C. *Legionella* identification can be carried out on GVPC *Legionella* medium (bioMérieux), which is a specific and selective medium that promotes the isolation of most *Legionella* species, in particular *L. pneumophila*. This medium makes it possible to inhibit the growth of Gram-positive bacteria, most Gram-negative bacteria, yeasts and molds, by virtue of an optimized mixture of three antibiotics. However, the current culture media contain activated carbon in order to adsorb the toxic compounds produced by the *Legionella*, or present in the medium (yeast extract, agar, etc.), or by autoclaving of the culture medium, which creates the formation of free radicals, which are also toxic for legionellae. These media are as a result black in color, which makes them unsuitable for the incorporation of chromogenic or fluorescent enzymatic substrates, which could nevertheless facilitate the reading of the medium.

The invention proposes to solve the problems of the prior art by providing a novel reaction medium for bacteria of the *Legionella* genus.

Surprisingly, the inventors have demonstrated that the use of siliceous compounds in a reaction medium allows rapid and easy detection of *Legionella*.

Before presenting the invention, the following definitions are given in order to provide better understanding of the invention. They are in no way limiting.

The term reaction medium is intended to mean a medium comprising all the elements necessary for the expression of a metabolism and/or for the growth of microorganisms such as legionellae.

The reaction medium may be solid, semi-solid or liquid. The term "solid medium" is intended to mean, for example, a gelled medium. Agar is the conventional gelling agent in microbiology for culturing microorganisms, but it is possible to use gelrite, gelatin, agarose or other natural or artificial gelling agents. The reaction medium according to the invention must allow the growth of legionellae.

The reaction medium may comprise one or more elements in combination, such as amino acids, carbohydrates, nucleotides, minerals, vitamins, etc.

The medium may also comprise a colorant. By way of indication, as a colorant, mention may be made of Evans blue, neutral red, an opacifier such as titanium oxide, nitroaniline, malachite green, brilliant green, one or more metabolic indicators, one or more metabolic regulators, etc.

The reaction medium may be a culture medium, a revealing medium or a culture and revealing medium. In the case of a revealing medium, the microorganisms are cultured before inoculation and, in the case of a culture and revealing medium, the revealing medium also constitutes the culture medium.

Those skilled in the art may also use a biplate, making it possible to readily compare two media, comprising various substrates or various selective mixtures, onto which the same biological sample will have been deposited.

The term selective mixture is intended to mean a mixture of compounds allowing the selective culture of particular microorganisms. In the context of the present invention, the selective mixture can allow the selective culture of legionellae. Such a medium comprises in particular the following compounds: glycine, polymyxin B sulfate, vancomycin or cefamandole, cycloheximide or anisomycin or else natamycin, alone or in combination. The selective medium can also allow the selective culture of certain *legionella* species, for instance *L. pneumophila*. In this case, the selective mixture comprises in particular the following compounds: glycine, polymyxin B sulfate, vancomycin or cefamandole, cycloheximide, anisomycin, natamycin, bromocresol purple, bromothymol blue, alone or in combination.

The term siliceous compound is intended to mean any compound containing the element silicon. Mention may be made, in a nonlimiting manner, of natural or synthetic zeolites, clays, preferably illite, moontmorillonite and preferably sepiolite, or else nonpolar silicas.

The term nonpolar silica is intended to mean one or more silica particles onto which have been grafted nonpolar chemical functions, most commonly alkylated chains having at least 2 carbon atoms. Preferably, they have 4 to 24 carbon atoms, even more preferably 18 carbon atoms (octadecyl), 8 carbon atoms (octyl) or 4 carbon atoms (butyl). Preferably, this nonpolar silica is an octadecyl silica or an octyl silica.

The term enzymatic substrate is intended to mean a molecule that can be metabolized by an enzyme, to give a product allow the direct or indirect detection of a microorganism. It may be a natural or synthetic substrate. The metabolism of the substrate will cause a variation in the physicochemical properties of the reaction medium or of the organism cells. This variation can be detected by physicochemical methods, in particular optical methods, by eye by the operator or by means of instruments, spectrometric methods, electrical methods, magnetic methods, etc. Preferably, it will be a variation in the optical properties, such as a modification of absorption, of fluorescence or of luminescence.

The term fluorogenic or chromogenic enzymatic substrate is intended to mean a molecule, the metabolism of which generates a product that has a fluorescence or a color different than the substrate.

In the context of the present invention, the enzymatic substrate is preferably chosen from oxidoreductase substrates and hydrolase substrates.

Preferably, this substrate is a nitroreductase, oxidoreductase, acetoacetyl-CoA reductase, dehydrogenase, superoxide dismutase, osidase, peptidase, nuclease or esterase substrate. As chromogenic substrate, mention may in particular be made of those based on alizarin, alpha-glucosidase substrates, and most particularly alizarin-alpha-glucoside.

As fluorogenic substrate, mention may be made of those based on coumarin, those described in patent EP 0641351 ("Enzymatic analysis using substrates that yield fluorescent precipitates", Haugland et al) or in patent application FR 07/55371, reductase substrates, and in particular nitroreductase substrates, and more preferably those described in patent application FR 07/55373 or in patent EP 1 124 986. As substrates for oxidoreductase enzymatic activity, mention may more particularly be made of reductase substrates and preferably nitroreductase substrates.

The introduction of a second enzymatic substrate, and in particular a second alpha-glucosidase substrate, into a medium already containing alizarin-alpha-glucoside makes it possible to increase the differentiation of the legionellae from the other genera which grow on the medium.

The term biological sample is intended to mean a clinical sample, derived from a specimen of bronchial, tracheal or pulmonary aspiration, of pleural fluid, of a bronchoalveolar lavage, a sputum specimen, a blood specimen or a lung biopsy specimen, and more rarely a specimen of joint or pericardial fluid; or a food sample. This sample may thus be liquid or solid and mention may be made, in a nonlimiting manner, of a clinical blood, plasma, urine or feces sample, nose, throat, skin, wound or cerebrospinal fluid specimens, or a food sample from water (drinking water).

The term environmental sample is intended to mean a water specimen, and mention may be made, in a nonlimiting manner, of: a water supply network, an air-conditioning system, a cooling tower, a sprayer, a mister.

In this respect, the invention relates, firstly, to a reaction medium for culturing and/or detecting and/or identifying bacteria of the *Legionella* genus, comprising at least one nonpolar silica. Preferably, said nonpolar silica is octadecyl silica. Preferably, said nonpolar silica is in combination with a clay, preferably sepiolite. Preferably, the octadecyl silica is in combination with sepiolite.

According to one preferred embodiment of the invention, said reaction medium also comprises an enzymatic substrate.

Preferably, said enzymatic substrate is a fluorogenic or chromogenic, preferably chromogenic, enzymatic substrate.

Preferably, said fluorogenic or chromogenic enzymatic substrate is an oxidoreductase substrate or a hydrolase substrate.

According to one preferred embodiment of the invention, the concentration of nonpolar silica is between 0.01 and 100 g/l, preferably between 1 and 5 g/l. In the case where the medium according to the invention comprises a nonpolar silica in combination with a clay, the concentration of clay is also between 0.01 and 100 g/l, preferably between 1 and 5 g/l.

According to one preferred embodiment of the invention, the reaction medium also comprises a selective mixture which allows the selective culture of bacteria of the *Legionella* genus.

Preferably, this selective mixture comprises glycine, polymyxin B sulfate, vancomycin, cycloheximide, anisomycin, bromocresol purple or bromothymol blue, alone or in combination.

The use of such a medium allows the selective detection of bacteria of the *Legionella* genus.

The medium according to the invention can also comprise a selective mixture which allows the selective culture of particular species of *Legionella*, such as *Legionella pneumophila*. This selective mixture then preferably comprises glycine, polymyxin 13 sulfate, vancomycin, a quinolone or a fluoroquinolone, cycloheximide, anisomycin, bromocresol purple or bromothymol blue, alone or in combination. The difference in selectivity can also be obtained by varying the concentration of glycine ranging from 2.5 g/l to 7.5 g/l (Glycine-containing selective medium for isolation of Legionellaceae from environmental specimens, Robert M. Wadowski and Robert B. Yee).

The invention also relates to the use of a reaction medium comprising at least one siliceous compound, for culturing, detecting and/or identifying bacteria of the *Legionella* genus. Preferably, said siliceous compound is a nonpolar silica and/or a clay. Preferably, said nonpolar silica is octadecyl silica. Preferably, said clay is sepiolite.

According to one preferred embodiment of the invention, the concentration of siliceous compound, in the reaction medium used, is between 0.01 and 100 g/l, preferably between 1 and 5 g/l. In the case where the reaction medium used comprises a combination of siliceous compounds, the concentration of each of the compounds is between 0.01 and 100 g/l, preferably between 1 and 5 g/l.

Finally, the invention relates to a method for detecting and/or identifying bacteria of the *Legionella* genus, characterized in that it comprises the following steps:
a) bringing a sample that may contain bacteria of the *Legionella* genus into contact with a reaction medium as defined above;
b) incubating, and
c) detecting the presence of bacteria of the *Legionella* genus.

The incubation is preferably carried out at a temperature between 30° C. and 50° C., and more preferably between 36° C. and 42° C. The legionellae are preferably detected by means of an alpha-glucosidase or oxidoreductase activity which makes it possible to obtain colored or fluorescent colonies. The colonies of the other genera, if they are not inhibited, are either colorless or different in color or identical in color or fluorescence to those of *Legionella*.

The incubation time allows growth of the bacteria of the *Legionella* genus in order to allow their detection. Without being limiting, an incubation of 48-72 h is suitable, but a shorter incubation is possible.

The BCYE medium (Feeley et al, J Clin Microbiol. 1979 10:437-41) was a medium which acted as a growth control.

2. Tests

The media were distributed into Petri dishes. The various *Legionella* strains were inoculated by three quadrant streaking. The dishes were incubated for 96 h at 37° C. in the presence of $CO_2$.

Readings were carried out after 72 and 96 h of incubation.

3. Results

The results are recorded in the table below:

|  |  | BCYE growth | | medium 1 growth | | medium 2 growth | | medium 3 growth | | medium 4 growth | |
|---|---|---|---|---|---|---|---|---|---|---|---|
|  |  | M | C | M | C | M | C | M | C | M | C |
| L. pneumophila | 72 h | 3 | 0.5+ | 3 | 1 | 2 | 0 | 2 | 0 | 3 | 1 |
| 07 10 139 | 96 h | 3 | 1 | 3 | 1.25 | 2 | 0 | 2 | 0 | 3 | 1 |
| L. pneumophila | 72 h | 3 | 0.5 | 3 | 0.75 | 3 | 0.25 | 3 | 0.25 | 3 | 0.75 |
| 07 10 146 | 96 h | 3 | 1 | 3 | 1 | 3 | 1 | 3 | 1 | 3 | 1 |
| L. pneumophila | 72 h | 3 | 0.75 | 3 | 1 | 1 | 0.75 | 1 | 0 | 3 | 1 |
| 07 10 138 | 96 h | 3 | 1 | 3 | 1.25 | 2 | 1.25 | 1+ | 0 | 3 | 1 |
| L. pneumophila | 72 h | 3 | 1 | 3 | 1.25 | 3 | 0.5 | 3 | 0.5 | 3 | 1 |
| 07 10 142 | 96 h | 3 | 1.25 | 3 | 1.25 | 3 | 0.5+ | 3 | 0.5+ | 3 | 1 |
| L. pneumophila | 72 h | 3 | 0.75 | 3 | 1 | veil | | 0 | 0 | 3 | 1 |
| 07 10 144 | 96 h | 3 | 1.25 | 3 | 1 | veil | | veil | | 3 | 1 |
| L. pneumophila | 72 h | 3 | 0.75 | 3 | 1.25 | 3 | 0.1 | 3 | 0.1 | 3 | 1.25 |
| 07 10 143 | 96 h | 3 | 1 | 3 | 1.25 | 3 | 0.5 | 3 | 0.5 | 3 | 1.25 |
| L. erythra | 72 h | 3 | 0.5 | 3 | 0.75 | 0 | 0 | 0 | 0 | 3 | 0.5+ |
| 04 12 069 | 96 h | 3 | 0.5 | 3 | 1 | 0 | 0 | 0 | 0 | 3 | 0.5+ |
| L. rubrilucens | 72 h | 3 | 0.5+ | 3 | 1 | veil | | 0 | 0 | 3 | 1 |
| 04 12 075 | 96 h | 3 | 0.75 | 3 | 1 | 2 | 0 | veil | | 3 | 1 |
| L. feelii | 72 h | 3 | 0.25 | 3 | 1 | 0 | 0 | 0 | 0 | 3 | 1 |
| 04 12 070 | 96 h | 3 | 0.25 | 3 | 1 | 0 | 0 | 0 | 0 | 3 | 1 |
| L. longbeachae | 72 h | 3 | 1 | 3 | 1 | 0 | 0 | 0 | 0 | 3 | 1 |
| 04 12 073 | 96 h | 3 | 1 | 3 | 1 | 0 | 0 | 0 | 0 | 3 | 1 |

M: mass; C: colonies
The notation "1", "2" or "3" in the M (mass) column indicates growth of the strain tested on 1, 2 or 3 quadrants; "0" indicates an absence of growth. The size of the colonies (C) is given in millimeters.

When this medium is used, the legionellae are preferably detected by means of an oxidoreductase activity which makes it possible to obtain colored or fluorescent colonies. The other bacteria are either inhibited, or colorless, or different in color or fluorescence, or identical in color or fluorescence to those of the legionellae.

The examples below are given by way of explanation and have no limiting nature. They will make it possible to understand the invention more clearly.

Example 1

Various strains of the *Legionella* genus were tested on 5 different media. The dishes are then read after 72 h and 96 h of incubation.

1. Media and Microorganisms

The medium having the following composition was used (composition in g/l):

yeast extract: 10 g/l
alpha-ketoglutaric acid: 1 g/l
ACES/KOH: 4/1.65 g/l
glycine: 3 g/l
cysteine hydrochloride: 0.4 g/l
ferric pyrophosphate: 0.25 g/l
glutathione: 5 g/1
agar: 17 g/l.

5 g/l of nonpolar silica (octadecyl silica, medium 1), 5 g/l of polar silica (silica gel, medium 2), 5 g/l of highly polar silica (3-aminopropyl silica, medium 3) or 5 g/l of nonpolar silica (octyl silica, medium 4) were added to this medium.

4. Interpretation

The media containing silicas of nonpolar nature allowed growth of all the strains tested, said growth being greater than the BCYE medium.

Example 2

Various strains of the *Legionella* genus were tested on 8 different media. The dishes were then read after 72 h and 96 h of incubation.

4. 1. Media and Microorganisms

The medium having the following composition was used (composition in g/l):

yeast extract: 10 g/l
alpha-ketoglutaric acid: 1 g/l
ACES/KOH: 4/1.65 g/l
glycine: 3 g/l
cysteine hydrochloride: 0.4 g/l
ferric pyrophosphate: 0.25 g/l
glutathione: 5 g/l
agar: 17 g/l.

1 g/l of nonpolar silica (octadecyl silica, medium T), or, respectively, 0.1, 0.5, 1, 2.5, 5, 7.5 or 10 g/l of sepiolite (media 1, 2, 3, 4, 5, 6 and 7) were added to this medium.

2. Tests

The media were distributed into Petri dishes. The various strains of *Legionella* were inoculated by three-quadrant streaking. The dishes were incubated for 96 h at 37° C. in the presence of $CO_2$.

Readings were carried out after 72 and 96 h of incubation,

3. Results
The results are recorded in the table below:

| | | T octadecyl silica g/l | | 1 | | 2 | | 3 | | 4 Sepiolite in g/l | | 5 | | 6 | | 7 | |
|---|---|---|---|---|---|---|---|---|---|---|---|---|---|---|---|---|---|
| | | 1 | | 0.1 | | 0.5 | | 1 | | 2.5 | | 5 | | 7.5 | | 10 | |
| | | M | C | M | C | M | C | M | C | M | C | M | C | M | C | M | C |
| L pneumophila | 72 h | 3 | 0.75 | 2 | 0 | 2 | 0 | 2 | 0 | 3 | 0.1 | 3 | 0.75 | 3 | 0.75 | 3 | 0.5 |
| 07 10 139 | 96 h | 3 | 0.75 | 2 | 0 | 2 | 0 | 2 | 0 | 3 | 0.1 | 3 | 0.75 | 3 | 0.75 | 3 | 0.5 |
| L pneumophila | 72 h | 3 | 1 | 2 | 0 | 2 | 0 | 3 | 0.25 | 3 | 0.25 | 3 | 0.75 | 3 | 0.75 | 3 | 1 |
| 07 10 143 | 96 h | 3 | 1.5 | 3 | 0.5 | 3 | 0.75 | 3 | 1 | 3 | 1 | 3 | 1.25 | 3 | 1.25 | 3 | 1.25 |
| L pneumophila | 72 h | 3 | 0.5 | 2 | 0 | 2 | 0 | 3 | 0.1 | 3 | 0.5 | 3 | 0.75 | 3 | 0.5 | 3 | 0.75 |
| 07 10 138 | 96 h | 3 | 0.75 | 2 | 0 | 2 | 0 | 3 | 0.25 | 3 | 0.5 | 3 | 1 | 3 | 0.75 | 3 | 1 |
| L pneumophila | 72 h | 3 | 0.75 | 3 | 0.5 | 3 | 0.5 | 3 | 0.5 | 3 | 0.75 | 3 | 1 | 3 | 0.75 | 3 | 0.5 |
| 07 10 142 | 96 h | 3 | 0.75 | 3 | 1 | 3 | 0.75 | 3 | 1 | 3 | 1.25 | 3 | 1.25 | 3 | 1 | 3 | 1 |
| L erythra | 72 h | 1 | 0 | 0 | 0 | 0 | 0 | 0 | 0 | 0 | 0 | 0 | 0 | 0 | 0 | 0 | 0 |
| 04 12 069 | 96 h | 1 | 0 | 0 | 0 | 0 | 0 | 0 | 0 | 0 | 0 | 0 | 0 | 0 | 0 | 0 | 0 |
| L rubrilucens | 72 h | 3 | 0.25 | 0 | 0 | 0 | 0 | 1 | 0 | 2 | 0 | 2 | 0 | 3 | 0.1 | 3 | 0.1 |
| 04 12 075 | 96 h | 3 | 0.5 | 0 | 0 | 0 | 0 | 1 | 0 | 2 | 0 | 2 | 0 | 3 | 0.75 | 3 | 0.5 |
| L feelii | 72 h | 3 | 0.5 | 0 | 0 | 0 | 0 | 0 | 0 | 2 | 0 | 3 | 0.5 | 3 | 0.5 | 3 | 0.75 |
| 04 12 070 | 96 h | 3 | 0.75 | 0 | 0 | 0 | 0 | 1 | 0 | 2 | 0 | 3 | 0.75 | 3 | 0.5 | 3 | 0.75 |
| L longbeachae | 72 h | 2 | 0 | 0 | 0 | 0 | 0 | 0 | 0 | 0 | 0 | 0 | 0 | 0 | 0 | 0 | 0 |
| 04 12 073 | 96 h | 3 | 0.25 | 0 | 0 | 0 | 0 | 0 | 0 | 0 | 0 | 0 | 0 | 0 | 0 | 0 | 0 |

Growth: M: mass; C: colonies
The notation "1", "2" or "3" in the M (mass) column indicates the growth of the strain tested on 1, 2 or 3 quadrants; "0" indicates an absence of growth. The size of the colonies (C) is given in millimeters.

4. Interpretation

The media containing sepiolite at concentrations of between 5 and 10 g/l allowed growth of all the *Legionella pneumophila*, said growth being substantially identical to the control medium.

Example 3

Various strains of the *Legionella* genus were tested on 3 different media. The dishes were then read after 72 h and 96 h of incubation.

1. Media And Microorganisms

The medium having the following composition was used (composition in g/l):

yeast extract: 10 g/l alpha-ketoglutaric acid: 1 g/l

ACES/KOH: 4/1.65 g/l glycine: 3 g/l cysteine hydrochloride: 0.4 g/l ferric pyrophosphate: 0.25 g/l glutathione: 5 g/l octadecyl silica: 1 g/l.

17 g/l of agar (medium T), 17 g/l of gelrite (medium T1) and 5 g/l of sepiolite and 17 g/1 of agar (medium T2) were added to this medium.

2. Tests

The media were distributed into Petri dishes. Various *Legionella* strains were inoculated by three-quadrant streaking. The dishes were incubated for 96 h at 37° C. in the presence of $CO_2$.

Readings were carried out after 72 and 96 h of incubation.

3. Results

The results are recorded in the table below:

| | T | T1 | T2 |
|---|---|---|---|
| Sepiolite g/l | 0 | 0 | 5 |
| Gelrite g/l | 0 | 17 | 0 |
| Agar g/l | 17 | 0 | 17 |

-continued

| | | growth | | growth | | growth | |
|---|---|---|---|---|---|---|---|
| | | M | C | M | C | M | C |
| *Legionella pneumophila* | 72 h | 3 | 1 | 3 | 2 | 3 | 1.25 |
| 07 10 139 | 96 h | 3 | 1.25 | 3 | 3 | 3 | 1.25 |
| *Legionella pneumophila* | 72 h | 3 | 1.25 | 3 | 1.5 | 3 | 1.25 |
| 07 10 138 | 96 h | 3 | 1.5 | 3 | 2 | 3 | 1.25 |
| *Legionella pneumophila* | 72 h | 3 | 0.75 | 3 | 1.25 | 3 | 1 |
| 07 10 142 | 96 h | 3 | 1 | 3 | 2 | 3 | 1 |
| *Legionella pneumophila* | 72 h | 3 | 0.25 | 3 | 1 | 3 | 0.75 |
| 07 10 147 | 96 h | 3 | 1 | 3 | 1.5 | 3 | 1 |
| *Legionella pneumophila* | 72 h | 3 | 0.25 | 3 | 1.25 | 3 | 0.75 |
| 07 10 149 | 96 h | 3 | 1 | 3 | 1.5 | 3 | 1 |
| *Legionella rubrilucens* | 72 h | 3 | 0.25 | 3 | 1.5 | 3 | 0.75 |
| 04 12 075 | 96 h | 3 | 0.5 | 3 | 1.5 | 3 | 0.75 |
| *Legionella feelii* | 72 h | 2 | 0 | 3 | 1.25 | 3 | 0.25 |
| 04 12 070 | 96 h | 3 | 0.25 | 3 | 1.5 | 3 | 0.75 |
| *Legionella longbeachae* | 72 h | 3 | 0.1 | 3 | 1 | 3 | 0.5 |
| 04 12 073 | 96 h | 3 | 0.75 | 3 | 1.25 | 3 | 0.75 |

The notation "1", "2" or "3" in the M (mass) column indicates growth of the strain tested on 1, 2 or 3 quadrants. The size of the colonies (C) is given in millimeters.

4. Interpretation

All the media tested here allowed growth of all the legionellae with large isolated colony sizes.

Example 4

Various strains of the *Legionella* genus were tested on a medium according to the invention comprising a fluorogenic substrate for nitroreductase, namely 2-(5'-fluoro-2'-nitrophenyl)benzothiazole. The dishes were then read after 72 h, 96 h and 120 h of incubation.

1. Media and Microorganisms

The medium having the following composition was used (composition in g/l):

yeast extract: 10 g/l alpha-ketoglutaric acid: 1 g/l

ACES/KOH: 4/1.65 g/l glycine: 3 g/l cysteine hydrochloride: 0.4 g/l
ferric pyrophosphate: 0.25 g/l
glutathione: 5 g/l
agar: 17 g/l
octadecyl silica: 1 g/l.

A stock solution of fluorogenic substrate 2-(5'-fluoro-2'-nitrophenyl)benzothiazole was prepared in a solvent of DMSO type at 50 g/l. A volume corresponding to a final concentration of 5 mg/l of substrate was added to said molten medium.

2. Tests

The media were poured into Petri dishes 55 mm in diameter, and then *Legionella* strains were inoculated by three-quadrant streaking from suspensions at 0.5 McFarland. The dishes were incubated at 37° C. for 5 days.

3. Results

The colonies formed were examined visually after 72, 96 and 120 hours of incubation. The fluorescence (read under a UV lamp at 366 nm) and also the intensity were noted.

The results are recorded in the table below:

1. Media and Microorganisms

The medium having the following composition was used (composition in g/l):
yeast extract: 10 g/l
alpha-ketoglutaric acid: 1 g/l
ACES/KOH: 4/1.65 g/l
glycine: 3 g/l
cysteine hydrochloride: 0.4 g/l
ferric pyrophosphate: 0.25 g/l
glutathione: 5 g/l
agar: 17 g/l
octadecyl silica: 1 g/l.

A stock solution of chromogenic substrate (alizarin-alpha-glucoside) was prepared in a solvent of DMSO type at 40 g/l. A volume corresponding to a final concentration of 50 mg/l of substrate was added to said molten medium, In the same way, a stock solution of iron citrate was prepared in osmosed water, and then the solution was filtered before being added to the medium at 100 mg/l.

|  |  | T | | | | | 1 = T + 5 mg/L of florescent substrate for nitroreductase | | | | |
|  |  | growth | | fluorescence | | | growth | | fluorescence | | |
|  |  | M | C | M | C | color | M | C | M | C | color |
|---|---|---|---|---|---|---|---|---|---|---|---|
| *Legionella* | 72 h | 3 | 1.25 | 0 | 0 | 0 | 3 | 0.75 | 0.5 | 0 | blue |
| *pneumophila* | 96 h | 3 | 2– | 0 | 0 | 0 | 3 | 1.5 | 2 | 2 | blue |
| 07 10 139 | 120 h | 3 | 2+ | 0 | 0 | 0 | 3 | 1.5 | 3 | 3 | blue |
| *Legionella* | 72 h | 3 | 1.25 | 0 | 0 | 0 | 3 | 0.75 | 1 | 0.5 | blue |
| *pneumophila* | 96 h | 3 | 1.25 | 0 | 0 | 0 | 3 | 1 | 2 | 2 | blue |
| 07 10 146 | 120 h | 3 | 1.5 | 0 | 0 | 0 | 3 | 1.25 | 1 | 3 | blue |
| *Legionella* | 72 h | 3 | 1.5 | 0 | 0 | 0 | 3 | 0.75 | 1 | 0 | blue |
| *pneumophila* | 96 h | 3 | 2 | 0 | 0 | 0 | 3 | 1.5 | 2 | 2 | blue |
| 07 10 138 | 120 h | 3 | 2 | 0 | 0 | 0 | 3 | 1.5 | 1 | 2 | blue |
| *Legionella* | 72 h | 3 | 1 | 0 | 0 | 0 | 3 | 0.75 | 1 | 0.1 | blue |
| *pneumophila* | 96 h | 3 | 1+ | 0 | 0 | 0 | 3 | 1 | 2 | 2 | blue |
| 07 10 142 | 120 h | 3 | 1+ | 0 | 0 | 0 | 3 | 1 | 2 | 3 | blue |
| *Legionella* | 72 h | 3 | 0.75 | 0 | 0 | 0 | 3 | 1 | 1 | 0 | blue |
| *pneumophila* | 96 h | 3 | 2– | 0 | 0 | 0 | 3 | 1.25 | 3 | 2 | blue |
| 07 10 144 | 120 h | 3 | 2 | 0 | 0 | 0 | 3 | 2 | 2 | 3 | blue |
| *Legionella* | 72 h | 3 | 1.5 | 0 | 0 | 0 | 3 | 1 | 0.5 | 0 | blue |
| *pneumophila* | 96 h | 3 | 2 | 0 | 0 | 0 | 3 | 1 | 2 | 2 | blue |
| 07 10 143 | 120 h | 3 | 2 | 0 | 0 | 0 | 3 | 1.25 | 1 | 3 | blue |
| *Legionella* | 72 h | 3 | 1 | 0 | 0 | 0 | 1 | 0 | 0.1 | 0 | blue |
| *erythra* | 96 h | 3 | 1 | 0 | 0 | 0 | 1 | 1 | 0 | 0.5 | blue |
| 04 12 069 | 120 h | 3 | 1 | 0 | 0 | 0 | 2 | 1 | 0.1 | 0.5 | blue |
| *Legionella* | 72 h | 3 | 1 | 0 | 0 | 0 | 3 | 0.5+ | 1 | 0 | blue |
| *rubilucens* | 96 h | 3 | 1 | 0 | 0 | 0 | 3 | 0.5+ | 2 | 1 | blue |
| 04 12 075 | 120 h | 3 | 1 | 0 | 0 | 0 | 3 | 0.75 | 2 | 2 | blue |
| *Legionella* | 72 h | 3 | 1 | 0 | 0 | 0 | 3 | 0.75 | 1 | 0.1 | blue |
| *feelii* | 96 h | 3 | 1 | 0 | 0 | 0 | 3 | 0.75 | 2 | 2 | blue |
| 04 12 070 | 120 h | 3 | 1 | 0 | 0 | 0 | 3 | 0.75 | 1 | 3 | blue |
| *Legionella* | 72 h | 3 | 1 | 0 | 0 | 0 | 3 | 0.5 | 0.5 | 0 | blue |
| *longbeachae* | 96 h | 3 | 1 | 0 | 0 | 0 | 3 | 0.5 | 0 | 1 | blue |
| 04 12 073 | 120 h | 3 | 1 | 0 | 0 | 0 | 3 | 0.5 | 0 | 1 | blue |

0 indicates either the absence of isolated colonies or the absence of fluorescence. The fluorescence intensities are read on a scale ranging from 0 (no fluorescence) to 4 (very intense fluorescence).

4. Interpretation

A medium according to the invention, comprising a fluorogenic substrate, allowed growth of all the strains tested, and easy detection of legionellae.

Example 5

Various strains of the *Legionella* genus were tested on a medium according to the invention comprising a chromogenic substrate for alpha-glucosidase, namely alizarin-alpha-glucoside. The dishes were then read after 72 h and 96 h of incubation.

2. Tests

The media were poured into Petri dishes 55 mm in diameter and then *Legionella* strains were inoculated by three-quadrant streaking from suspensions at 0.5 McFarland. The dishes were incubated at 37° C. for 4 days.

3. Results

The colonies formed were examined visually after 72 and 96 hours of incubation. The colorations and also the intensities were noted.

The results are recorded in the table below:

|  |  | Medium T | | | | | | Medium 1<br>50 mg/l alizarin-alpha-Glu +<br>100 mg/l iron citrate | | | | | |
|  |  | growth | | intensity | | color | | growth | | intensity | | color | |
| Strains | Inc. time | M | C | M | C | M | C | M | C | M | C | M | C |
| --- | --- | --- | --- | --- | --- | --- | --- | --- | --- | --- | --- | --- | --- |
| *L. pneumophila* 07 10 144 | 72 h | 3 | 0.5+ | 0 | 0 | 0 | 0 | 0 | 0 | 0 | 0 | 0 | 0 |
|  | 96 h | 3 | 0.75 | 0 | 0 | 0 | 0 | 0 | 0 | 0 | 0 | 0 | 0 |
| *L. pneumophila* 07 10 146 | 72 h | 3 | 0.75 | 0 | 0 | 0 | 0 | 0 | 0 | 0 | 0 | 0 | 0 |
|  | 96 h | 3 | 1+ | 0 | 0 | 0 | 0 | 2 | 0 | 0.5 | 0 | P | 0 |
| *L. pneumophila* 07 10 142 | 72 h | 3 | 1+ | 0 | 0 | 0 | 0 | 3 | 0.50 | 1 | 1 | P | P |
|  | 96 h | 3 | 1.25 | 0 | 0 | 0 | 0 | 3 | 0.75 | 1.5 | 1.5 | P | P |
| *L. pneumophila* 07 10 141 | 72 h | 3 | 1 | 0 | 0 | 0 | 0 | 3 | 0.10 | 2 | 0 | Pvi | 0 |
|  | 96 h | 3 | 1.25 | 0 | 0 | 0 | 0 | 3 | 0.75 | 2 | 1 | Pvi | Pvi |
| *L. pneumophila* 07 10 139 | 72 h | 3 | 0.75 | 0 | 0 | 0 | 0 | 2 | 0 | 1.5 | 0 | Pvi | 0 |
|  | 96 h | 3 | 1 | 0 | 0 | 0 | 0 | 2 | 0 | 1.5 | 0 | Pvi | 0 |
| *L. jordanis* 04 09 055 | 72 h | 3 | 1.25 | 0 | 0 | 0 | 0 | 3 | 0.10 | 2 | 0.5 | Vi | Vi |
|  | 96 h | 3 | 1.25 | 0 | 0 | 0 | 0 | 3 | 0.25 | 2 | 1 | Vi | Vi |
| *L. erythra* 04 12 069 | 72 h | 3 | 0.75 | 0 | 0 | 0 | 0 | 0 | 0 | 0 | 0 | 0 | 0 |
|  | 96 h | 3 | 1+ | 0 | 0 | 0 | 0 | 0 | 0 | 0 | 0 | 0 | 0 |
| *L. rubrilucens* 04 12 075 | 72 h | 3 | 1+ | 0 | 0 | 0 | 0 | 2 | 0 | 1 | 0 | P | 0 |
|  | 96 h | 3 | 1.25 | 0 | 0 | 0 | 0 | 2 | 0 | 1.5 | 0 | Vi | 0 |
| *L. longbeachae* 04 12 073 | 72 h | 3 | 1+ | 0 | 0 | 0 | 0 | 0 | 0 | 0 | 0 | 0 | 0 |
|  | 96 h | 3 | 1.25 | 0 | 0 | 0 | 0 | 0.9 | 0.50 | 0.5 | 0 | P | 0 |
| *L. feelii* 04 12 070 | 72 h | 3 | 1 | 0 | 0 | 0 | 0 | 3 | 0.10 | 0.5 | 0 | P | 0 |
|  | 96 h | 3 | 1+ | 0 | 0 | 0 | 0 | 3 | 0.25 | 0.5 | 0 | P | 0 |

0 indicates either the absence of growth, or the absence of isolated colonies, or the absence of coloration. The coloration intensities were read on a scale ranging from 0 (no coloration) to 4 (very strong intensity). The colors vary from pink (denoted P) to violet (Vi), passing through Pvi (pink/violet).

4. Interpretation

A medium according to the invention, comprising a chromogenic substrate, allowed growth of 8/10 strains tested, and easy detection of legionellae via the appearance of a pink-to-violet coloration of the mass and of the colonies.

The invention claimed is:

1. A culture medium for detecting and/or identifying at least one species of the *Legionella* genus, comprising:
    elements necessary for the growth of the *Legionella* species; and
    at least one nonpolar silica having silica particles onto which has been grafted a nonpolar chemical function, the nonpolar silica being at a concentration between 0.01 and 100 g/l.

2. The culture medium as claimed in claim 1, further comprising a fluorogenic or chromogenic enzymatic substrate.

3. The culture medium as claimed in claim 2, wherein said fluorogenic or chromogenic enzymatic substrate is an oxidoreductase substrate or a hydrolase substrate.

4. The culture medium as claimed in claim 1, further comprising a selective mixture allowing the selective culture of the *Legionella* species.

5. A method for detecting and/or identifying at least one species of the *Legionella* genus, comprising:
    a. bringing a sample into contact with a culture medium;
    b. incubating the sample and the culture medium; and
    c. detecting the presence of the *Legionella* species when present in the sample,
    wherein the culture medium comprises:
        elements necessary for the growth of the *Legionella* species; and
        at least one nonpolar silica having silica particles onto which has been grafted a nonpolar chemical function, the nonpolar silica being at a concentration between 0.01 and 100 g/l.

6. The method as claimed in claim 5, wherein the culture medium further comprises a clay.

7. The method as claimed in claim 5, wherein the culture medium further comprises a fluorogenic or chromogenic enzymatic substrate.

8. The method as claimed in claim 7, wherein said fluorogenic or chromogenic enzymatic substrate is an oxidoreductase substrate or a hydrolase substrate.

9. The method as claimed in claim 5, wherein the culture medium further comprises a selective mixture allowing the selective culture of the *Legionella* species.

10. The culture medium as claimed in claim 1, wherein the concentration of said nonpolar silica is between 1 and 5 g/l.

11. The method as claimed in claim 5, wherein the concentration of said nonpolar silica is between 1 and 5 g/l.

12. The culture medium as claimed in claim 4, wherein the selective mixture allows for the selective culture of *L. pneumophila*.

13. The method as claimed in claim 9, wherein the selective mixture allows for the selective culture of *L. pneumophila*.

14. The culture medium as claimed in claim 1, wherein the elements necessary for the growth of the *Legionella* species include yeast extract, ACES buffer, L-cysteine, and iron.

15. The method as claimed in claim 5, wherein the elements necessary for the growth of the *Legionella* species include yeast extract, ACES buffer, L-cysteine, and iron.

16. The method as claimed in claim 5, wherein step (b) comprises culturing the *Legionella* species when present in the sample.

17. The culture medium as claimed in claim 1, wherein the culture medium is a gelled medium.

18. The culture medium as claimed in claim 1, wherein the nonpolar chemical function is an alkylated chain having from 4 to 24 carbon atoms.

19. The culture medium as claimed in claim 1, wherein the nonpolar silica is at least one of an octadecyl silica or an octyl silica.

20. The method as claimed in claim 5, wherein the nonpolar chemical function is an alkylated chain having from 4 to 24 carbon atoms.

21. The method as claimed in claim 5, wherein the nonpolar silica is at least one of an octadecyl silica or an octyl silica.

22. The culture medium as claimed in claim 1, wherein the culture medium does not contain activated carbon.

23. The method as claimed in claim 5, wherein the culture medium does not contain activated carbon.

* * * * *